Figure 1:
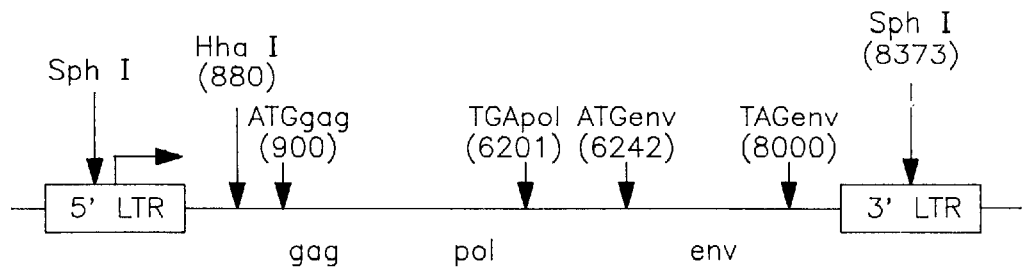
Figure 2:
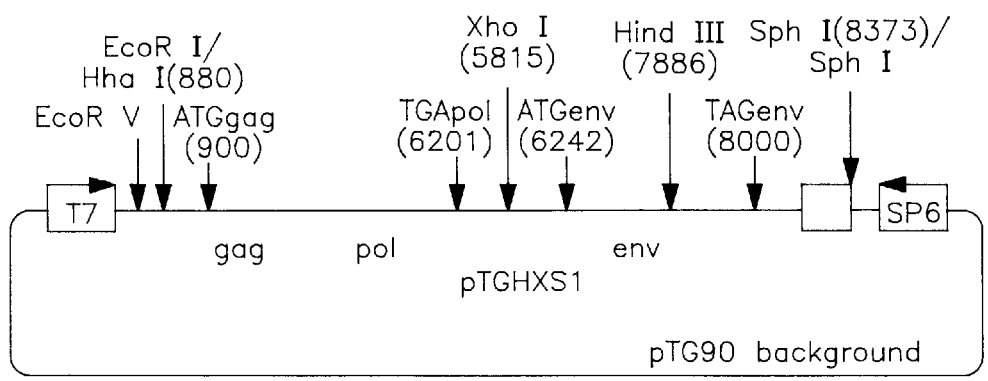
Figure 3:
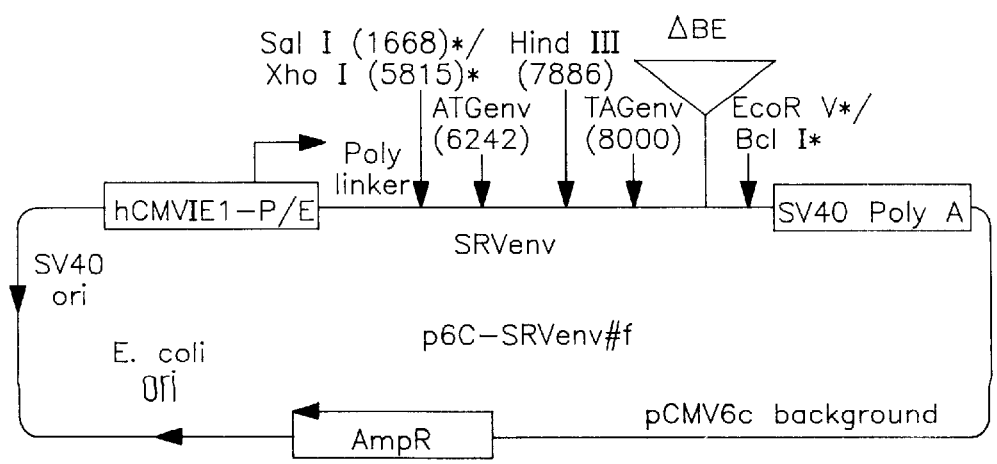

United States Patent
Khan et al.

Patent Number: 5,932,467
Date of Patent: Aug. 3, 1999

[54] RETROVIRAL VECTORS PSEUDOTYPED WITH SRV-3 ENVELOPE GLYCOPROTEIN SEQUENCES

[75] Inventors: Mohammad Ayub Khan, Chomedey Laval, Canada; Robert O. Ralston, The Woodlands, Tex.; John E. Murphy, Oakland, Calif.

[73] Assignee: Chiron Corporation, Emeryville, Calif.

[21] Appl. No.: 08/726,346

[22] Filed: Oct. 3, 1996

Related U.S. Application Data

[60] Provisional application No. 60/004,829, Oct. 5, 1995.

[51] Int. Cl.⁶ .............................. C12N 7/00; C12N 15/00; C12P 21/04; A01N 63/00
[52] U.S. Cl. .................................... 435/235.1; 435/172.3; 435/69.6; 435/236; 424/93.2; 424/207.1
[58] Field of Search .............................. 435/172.3, 235.1, 435/69.6, 236; 424/93.2, 207.1

[56] References Cited

PUBLICATIONS

Koo H. et al., Pseudotyped REV/SRV retroviruses reveal restrictions to infection and host range within members of the same receptor interference group, Virology 205:345–351, 1994.

Bosselman R. et al., Replication–defective chimeric helper proviruses and factors affecting generation of competent virus:Expression of Molony Murine Leukemia Virus structural genes via the metallothionein promoter, Mol. Cell. Biol. 7(5):1797–1806, May 1987.

Miller A. et al. Improved retroviral vectors for gene transfer and expression, Biotechniques 7(9):980–990, 1989.

Fan H. Murine Leukemia Viruses, in Encyclopedia of Virology v2, ed. Webster R. and Granoff A., Academic Press:883–890, 1994.

Moolton, Curability of Tumors Bearing Herpes Thymidine Kinase Genes Transferred by Retroviral Vectors, 1990, J Natl Cancer Inst 82: 297–300.

Rhee, Preassembled Capsids of Type D Retroviruses Contain a Signal Sufficient for Targeting Specifically to the Plasma Membrane, 1990, J Virol 64:3844–52.

Jensen, Isolation and Propagation of a Virus from a Spontaneous mammary Carcinoma of a Rhesus Monkey, 1970, Cancer Res 30:2388–93.

Wang, Cell–Surface Receptor for Ecotropic Murine Retroviruses is a Basic Amino–acid Transporter, 1991, Nature 352:729–31.

Rosen, Gene Therapy for Cancer, 1992, JAMA 268:2416–19.

Wolff, Grafting Fibroblasts Genetically Modified to Produce L–dopa in a Rat Model of Parkinson Disease, 1989, Proc Natl Acad Sci 86:9011–14.

Kasid, Human Gene Transfer: Characterization of Human Tumor–Infiltrating Lymphocytes as Vehicles for Retroviral–mediated Gene Transfer in Man, 1990, Proc Natl Acad Sci 87:473–477.

Rosenberg, Immunotherapy and Gene Therapy of Cancer, 1991, Cancer Res (Supp) 51:4074s–79s.

Anderson, Human Gene Therapy, 1992, Science 256:808–13.

(List continued on next page.)

*Primary Examiner*—Ponnathapura Achutamurthy
*Assistant Examiner*—Hankyel T. Park
*Attorney, Agent, or Firm*—Luann Cserr; Norman J. Kruse; Robert P. Blackburn

[57] ABSTRACT

Cells producing recombinant retroviral particles are provided. The cells contain a first vector having a coding region encoding retroviral LTRs and a packaging signal under the control of an expression control system, a tRNA binding site located upstream from the packaging signal and origin of second strand DNA synthesis located downstream from the packaging signal. The cells also contain a second vector having a coding region encoding retroviral capsid proteins gag and pol under the control of an expression control system and a third vector having a coding region encoding a simian type D retrovirus envelope glycoprotein under the control of an expression control system.

11 Claims, 1 Drawing Sheet

OTHER PUBLICATIONS

Levine, Towards Improved Cancer Diagnosis and Treatment Founded on Current Developments in the Basic Sciences: Options for Intensified European Efforts, 1991, Eur J Cancer 27:936–39.

Culver, In Vivo Gene Transfer with Retroviral Vector–Producer Cells for Treatment of Experimental Brain Tumors, 1992, Science 256:1550–52.

Rhodes, Inhibition of Heterologous Strains of HIV by Antisense RNA, 1991, AIDS 5:145–51.

Von Ruden, Inhibition of Human T–Cell Leukemia Virus Type I Replication in Primary Human T Cells that Express Antisense RNA, 1989, J Virol 63:677–82.

Giovannangeli, Single–Stranded DNA as a Target for Triple–Helix Formation, 1991, J Am Chem Soc: 113:7775–77.

Bosselman, Replication–Defective Chimeric Helper Proviruses and Factors Affecting Generation of Competent Virus: Expression of Moloney Murine Leukemia Virus Structural Genes via the Metallothionein Promoter, 1987, Mol and Cell Biol 7:1797–1806.

Markowitz, A Safe Packaging Line for Gene Transfer: Separating Viral Genes on Two Different Plasmids, 1988, J Virol 62:1120–24.

Dougherty, New Retrovirus Helper Cells with Almost No Nucleotide Sequence Homology to Retrovirus Vectors, 1989, J Virol 63:3209–12.

Miller, Improved Retroviral Vectors for Gene Transfer and Expression, 1989, BioTechniques 7:980–90.

Kim, Transport of Cationic Amino Acids by the Mouse Ecotropic Retrovirus Receptor, 1991, Nature 352:725–28.

Oldfield, Gene Therapy for the Treatment of Brain Tumors Using Intra–Tumoral Transduction with the Thymidine Kinase Gene and Intravenous Ganciclovir, 1993, Human Gene Therapy 4:39–69.

Neda, Chemical Modification of an Ecotropic Murine leukemia Virus Results in Redirection of its Target Cell specificity, 1991, J Biol Chem 266:14143–46.

Kasahara, Tissue–Specific Targeting of Retroviral Vectors Through Ligand–Receptor Interactions, 1994, Science 266:1373–76.

Deminie, Functional Exchange of an Oncoretrovirus and a Lentivirus Matrix Protein, 1994, J Virol 68:4442–49.

Miller, Targeted Vectors for Gene Therapy, 1995, FASEB J 9:190–99.

Von Kalle, Increased Gene Transfer into human Hematopoietic Progenitor Cells by Extended In Vitro Exposure to a Pseudotyped Retroviral Vector, 1994, Blood 84:2890–97.

Gardner, Chapter 5: The Simian Retroviruses SIV and SRV in The Retroviridae, vol. 3, 1994, Jay A Levy ed, Plenum Press, New York.

Barker, Molecular Cloning of the Mason–Pfizer Moneky Virus Genome: Biological Characterization of Genome Length Clones and Molecular Comparisons to Other Retroviruses, 1986, Virology 153:201–14.

Sonigo, Nucleotide Sequence of Mason–Pfizer Monkey Virus: An Imumunosuppressive D–Type Retrovirus, 1986, Cell 45:375–85.

Power, Nucleotide Sequence of SRV–1, a Type D Acquired Immune Deficiency Syndrome Retrovirus, 1986, Science 231:1567–72.

Marracci, Simian AIDS Type D Serogroup 2 Retrovirus: Isolation of an Infectious Molecular Clone and Sequence Analyses of its Envelope Glycoprotein Gene and 3' Long Terminal Repeat, 1995, J Virol 69:2621–28.

Sommerfelt, Expression of Simian Type D Retroviral (Mason–Pfizer Monkey Virus) Capsids in Insect Cells Using Recombinant Baculovirus, 1993, Virology 192:298–306.

Koo, Pseudotyped REV/SRV Retroviruses Reveal Restrictions to Infection and Host Range within Members of the Same Receptor Interference Group, 1994, Virology 205:345–51.

RETROVIRAL VECTORS PSEUDOTYPED WITH SRV-3 ENVELOPE GLYCOPROTEIN SEQUENCES

CROSS-REFERENCE TO RELATED APPLICATION

This application is related to provisional patent application Ser. No. 60/004,829, filed Oct. 5, 1995, from which priority is claimed under 35 U.S.C. §119(e)(1) and which is incorporated herein by reference in its entirety.

BACKGROUND OF THE INVENTION

FIELD OF INVENTION

This invention relates to pseudotyped viral vectors.

INTRODUCTION

Retroviral-mediated gene transfer, based upon ex vivo transduction of target cells, is known and has recently been employed in humans. The ability to target delivery and expression of selected genes or nucleic acid sequences into desirable tissue cells in an in vivo setting using retroviral vectors would be advantageous, making possible the widespread use of retroviral vectors for safe and effective treatment of genetic disorders, tumors and viral infections. Genetic disorders are the diseases resulting from lesions in genes and may include, for example, hematopoietic and bone marrow disorders, metabolic disorders resulting from defects in liver enzymes and diseases of the central nervous system. Potential clinical applications are thus numerous for such technology.

For some diseases, introduction of a functional homolog of the defective gene and production of even small amounts of the gene product could have a beneficial effect. Other diseases may require a specific amount of gene product to be produced at a specific time, typically in response to a physiological signal (regulated gene expression). An example of such diseases is diabetes, where insulin production requires such regulated gene expression. In such cases gene replacement, rather than gene augmentation which is currently in practice, would be indicated. Otherwise attempts can be made to correct the underlying genetic defect by using genes along with their native regulatory switches (gene augmentation). In other cases, where it is not necessary to correct the genetic lesion in the cell type that exhibits the defect, the gene may be introduced into a different cell type. This is usually true for genes either encoding secretory proteins or enzymes which catalyze the production of secretory products. An example is the case of Parkinson disease where retrovirally transduced fibroblasts encoding tyrosine hydroxylase and capable of making dopamine were intracerebrally implanted in rats. See Wolff, *Proc. Natl. Acad. Sci. USA* 86:9011–15(1989). However, most genetic diseases require that the defective gene be replaced in the relevant cell type.

Because malignancies appear to result from a number of genetic lesions, both inherited and acquired, which appear to activate oncogenes and/or inactivate tumor suppressor genes, gene therapy applications to treat tumors can take several approaches. One strategy is to enhance the cytotoxic effects of the body's natural defense mechanisms against tumor cells, for example using tumor infiltrating lymphocytes by expressing certain gene products. See for example, Kasid, *Proc. Nat. Acad. Sci. USA* 87:473–77(1990); Rosenberg, *Cancer Res. Supp.* 51:50745–50795(1991); Rosenberg, *J. Am. Med. Assn.* 268:2614–19(1992);

Anderson, *Science* 256:808–13(1992). Two second approach is directed toward inhibiting the activity of dominantly acting oncogenes. See Tubiana, *Eur. J. Cancer* 27:936–39(1991). Another strategy involves targeted delivery into tumor cells of the genes encoding toxic products or genes conferring sensitivity to toxic drugs. Thymidine kinase gene of the herpes simplex virus (HSV-tk) is exemplary. See Moolten and Wells, *J. Natl. Cancer Inst.* 82:297–300(1990) and Culver, *Science* 256:1550–52(1992). Retroviral vectors transducing HSV-tk gene into tumor cells enhance the incorporation of nucleoside analogs such as acyclovir and ganciclovir and thereby exhibit tumoricidal effect upon administration of these drugs.

Gene therapy also finds utility in the treatment of virally induced conditions, such as HIV and HTLV-I infections. The regulatory proteins or response elements of HIV and HTLV-I necessary for virus production are potential targets. Mutants of these proteins could be introduced to compete with the native viral proteins. In addition, antisense RNAs complementary to retroviral RNAs are being employed to specifically inhibit replication of HIV and HTLV-I See Rhodes and James, *AIDS* 5:145–51(1991); von Rueden and Gilboa, *J. Virol.* 63:677–82(1989). Retroviral vectors carrying HIV-specific antisense sequences or ribozymes could be used to inhibit expression of HIV for cellular immunization. Triple stranded RNA complexes, in which double-stranded RNA is locked into conformation by a third strand could prove an effective way of silencing viral gene expression by designing retroviral vectors encoding an antisense and an anti parallel triple stranded RNA on a single molecule from a retroviral vector. See Giovannangeli, *J. Am. Chem. Soc.* 113:7775–77(1991).

Retroviral vectors offer advantages over other viral gene transfer vehicles and other gene transfer methods including, for mammalian systems, electroporation, $CaPO_4$ precipitation, DEAE-dextran, direct DNA injection and lipofection. Retroviruses carry genetic information in the RNA form, reverse transcribing a DNA form upon infection that efficiently integrates into the genomic DNA of the infected cell and thereby offer stable propagation in the progeny cells. Retroviral integration is site specific with respect to viral ends, and the provirus is usually intact and colinear with the viral genome, i.e., the LTR-gag-pol-env-LTR gene order is maintained by the provirus. This reduces the possibility of DNA rearrangements and/or deletions, as is commonly observed with random pathway integration. Cells infected with replication defective retroviral vectors do not express viral proteins and thus are not susceptible to immune clearance. In addition, efficiency of gene transfer and stable expression in some dividing cells is very high with such vectors. For these reasons these vectors have been approved for use in human gene therapy.

Typical retroviral vector production systems consist of two components. A replication defective retroviral vector carries the gene or genes of interest and typically also carries a marker gene conferring upon infected cells a selectable advantage or a molecular tag for cell sorting. Since the retroviral genes (gag, pol, and env) have been deleted from these vectors to accommodate the foreign sequences and to arrest the replication competency of the vectors for safety reasons, helper constructs provide these viral structural proteins in trans to allow packaging of the vector into recombinant viral particles capable of infecting target cells.

The use of replication-competent, wild-type retroviruses as helper viruses for replication-defective vectors is highly undesirable because many of these retroviruses (including murine leukemia virus; MuLV) cause disease in animals, including primates. Packaging cell lines carrying deletions in the packaging signal have been developed and their use explored as the provider of the requisite in trans function. To further reduce the risk of generating wild-type replication competent virus, cell lines with two separate packaging constructs, one expressing gag and pol proteins, and another expressing the env protein, have been produced. See Bosselman, *Mol. Cell. Biol.* 7:1797–1806(1987); Markowitz, *J. Virol.* 62:1120–24(1988); and Dougherty, *J. Virol.* 63:3209–12(1989). Most known packaging constructs do not have LTRs, but use heterologous promoters and other regulatory sequences to express viral proteins. Since the packaging signal of MuLV is extended into the 5' gag region, the gag ATG codon has been mutated in the new generation vectors to further reduce the possibility of generating a replicating virus through homologous recombination. A. D. Miller and G. J. Rosman, *BioTechniques* 7(9):980–990 (1989).

While ex vivo therapeutic regimens have found success in treating certain genetic disorders, other disorders must be treated using an in vivo therapeutic approach because they affect cell types not easily isolated. The packaged vector should not be inactivated by specific host humoral or cellular immune responses or by non-specific responses such as complement or other blood factors. In such applications, it is also desirable that the retroviral vector infects only the cells in which the defect manifests itself or the expression of the therapeutic gene should be controlled by regulatory elements that target expression to the relevant cell type.

Retroviruses are classified according to their host range. For example, ecotropic murine retroviruses such as MuLV (MuLV-E)infect only murine cells. Xenotropic murine retroviruses such as MuLVs (MuLV-X) infect non-murine cells. Amphotropic murine retroviruses such as MuLVs (MuLV-A) infect both murine and non-murine cells, including human cells. This host range and cell tropism is determined primarily by the viral envelope protein and the availability of specific receptor proteins on the host cells. For example, the envelope protein (gp70) of Moloney MuLV-E interacts with a cationic amino acid transporter protein that serves as the host cell receptor. See Kim, *Nature* 352:725–28(1991). Because the receptor proteins of MuLV-E, -X, and -A are widely distributed among various tissue, vectors displaying these MuLV envelope proteins can infect virtually any dividing cell type of appropriate species and are tissue non-specific. Moloney murine leukemia virus (MoMuLV) has been employed with some success in vitro retroviral targeting experiments to limit the cells infected to those in which the defect manifests itself. Local administration of packaging (producer) cells producing MoMuLV vector into brain tumor tissue has been attempted. E. H. Oldfield, Clinical Protocals, "Gene Therapy for the Treatment of Brain Tumors Using Intra-Tumoral Transduction with the Thymidine Kinase Gene and Intravenous Gancyclovir," *Human Gene Therapy* 4:39–69(1993).

One approach to modifying the tissue-infecting capacity of retroviral vectors to achieve viral targeting involves use of bivalent, streptavidin-linked antibodies. A second approach involves chemical coupling of ligand to the viral env proteins. By coupling the env protein to lactose, the protein becomes an artificial asialoglycoprotein which is internalized by specific receptors on hepatocyte cells. See Neda, *J. Biol. Chem.* 226:14143–46(1991). These approaches result in low infection efficiency. A third approach involves mutation of the receptor recognition region of the env gene. For instance, an engineered MoMuLV-E vector bearing a chimeric erythropoietin-envelope (EPO-envelope) protein on its surface has exhibited infectivity for cells that bear the EPO receptor, both of murine and human origin. See Kasahara, *Science* 266:1373–76(1994). This chimeric construct had an EPO encoding sequence substituted for the N-terminal region of the env gene, and, although the chimeric MoMuLV-E construct exhibited tissue targeting, it required complementation from the wild type env protein.

Many retroviruses, such as MuLV, are unable to infect non-dividing cells such as monocytes and macrophages, which are important targets for gene transfer and gene therapy applications. For instance, attempts are being made to incorporate into MuLV vector system the capability of primate lentiviruses (HIV) to infect nondividing cells. See for example Deminie, *J. Virol.* 68:4442–49(1994) and references cited therein. In addition, recent attention has focused on the possible use of Type D retroviruses as gene therapy vectors since the natural targets of Type D viruses are different types of primate hematopoietic cells. Efforts are underway both to construct SRV homologous vector system and to explore the use of SRV envelope protein to pseudotype existing MuLV based retroviral vectors. This later approach has been employed to increase the efficiency of gene transfer by MuLV vectors using Gibbon Ape Leukemia Virus (GALV) envelope protein. See Kalle, *Blood* 84:2890–97(1994) and Miller, *FASEB J.* 9:190–99(1995).

Five distinct neutralization serotypes of exogenously transmitting simian type D retroviruses (SRV stands for simian retrovirus) are indigenous to Asian macaques monkeys and two related endogenous viral sequences have been defined. A distinguishing characteristic of these viruses is their morphology and ability to chronically infect human cells. In contrast to some other oncogenic retroviruses, SRV have not been shown to cause cancer (even though one member, SRV-3, was isolated from a female rhesus monkey breast carcinoma; see Jensen, *Cancer Res.* 30:1388–2393 (1970)), and only one member of the genus, SRV-2, has recently been shown to have some cell-transforming capacity in vitro. In addition, no bona fide infection with SRV is known in humans. See Gardner, "The Simian Retroviruses: SIV and SRV" in "The Retroviridae" Vol. 3, Levy, J. A. ed., Plenum Press, New York, 1994. The genome of the prototype virus, originally known as Mason-Pfizer monkey virus (MPMV) and now called SRV-3, has been molecularly cloned and characterized. Barker, *Virology* 153:201–14 (1986). A reconstructed sequence of the SRV-3 provirus has also been disclosed; see Sonigo, *Cell* 45:375–85(1986). The sequences of SRV-1 and SRV-2 have also been elucidated (Power, *Science* 231:1567–72(1986) and Marracci, *J. Virol.* 69:2621–28(1995)). For a detailed description of this group of simian retroviruses, see Gardner, "The Simian Retroviruses: SIV and SRV" in "The Retroviridae" Vol. 3, Levy, J. A. ed., Plenum Press, New York, 1994. The gag-pro-pol genes encoding the capsid proteins of SRV-3 have been expressed in insect cells using a recombinant baculovirus expression vector. See Sommerfelt, *Virology* 192:298–306 (1993). Expression of these capsids resulted in a proportion of particles assembling at the membrane, similarly to Type C retroviruses, and within the insect cell cytoplasm, the characteristic assembly site in Type D retroviruses. See Rhee, *J. Virol.* 64:3844–52(1990). Assembly and release of capsids in the absence of env gene expression confirmed previous observations that this gene product does not play an essential role in these processes. However, the released particles are non-infectious.

It would be advantageous to increase efficiency of gene transfer into different hematopoietic cells by pseudotyping retroviral vectors useful in gene therapy with desirable SRV envelope proteins (wild type or chimeric proteins) which confer modified host range or tissue tropism. SNV-based vectors pseudotyped with spleen necrosis virus (SNV), feline endogenous virus (RD114), and baboon endogenous virus (BaEV) specificities have been generated to study the host range conferred by the envelope glycoproteins of these three viruses, which share a common cellular receptor yet display slightly different host ranges. See Koo, *Virology* 205:345–51(1994).

SUMMARY OF THE INVENTION

The invention includes pseudotyped retroviral vector particles, comprising (1) as viral RNA in the particle, a recombinant vector comprising a retroviral LTR and packaging signal regions and further comprising a coding region encoding a non-retroviral protein or genetic control sequence located downstream of the packaging signal or encoding a heterologous retroviral seqeunce useful in treatment of disease, such as an HIV protein sequence; (2) as capsid proteins, non-SRV capsid proteins; and (3) as envelope glycoproteins, SRV envelope glycoproteins.

The invention also includes packaging cell lines for production of these pseudotyped retroviral vector particles. The vector virus particle is produced in a cell comprising (1) a first vector having a coding region encoding MuLV LTR and packaging signal regions and a non-MuLV protein or genetic control sequence, the non-MuLV sequence being located downstream of the packaging signal, (2) a second vector having a coding region encoding MuLV capsid proteins, and (3) a third vector having a coding region encoding SRV envelope glycoproteins, where any of the vectors can optionally be incorporated into a chromosome of the cell.

BRIEF DESCRIPTION OF THE DRAWINGS

The invention now being generally described, the same will be better understood by reference to the following detailed description when considered in combination with the drawings that form part of this specification, wherein:

FIG. 1 is a schematic diagram showing an exemplary starting molecular clone containing full-length SRV-3 provirus (for example, pSHARM 15).

FIG. 2 is a schematic diagram showing an exemplary intermediate cloning product containing a 5' HhaI and 3' SphI fragment of the SRV-3 provirus cloned into plasmid pTG90, including a XhoI site (N#5815) introduced by site-specific muted genesis, the product plasmid being referred to pTGHSX1.

FIG. 3 is an exemplary product plasmid capable of expressing SRV env expression system. In this figure hCMVIE-1-P/E is human cytomegalovirus immediate early promoter/enhancer; SV40 Poly A is polyadenylation signal from SV40 virus; ori is origin of replication in the respective host; Δ is deletion and * shows the restriction site is lost; and polylinker consists of 5' EcoR I-Sma I-Xba I-Cla I-BamH I-Sal I 3', where EcoR I is 3' to hCMVIE1-P/E and Sal I is 5' to SRV env.

DETAILED DESCRIPTION

The methods and compositions of this invention accomplish the foregoing in two ways. By pseudotyping a non-SRV retrovirus which is desirable for use in gene therapy (eg. MuLV) with the env gene of SRV, SRV's ability to infect a wide variety of primate non-lymphoid and lymphoid cells, including B and T lymphocytes, is conferred onto the non-SRV. "Vector construct", "retroviral vector", "recombinant vector", and "recombinant retroviral vector" refers to a nucleic acid construct which carries, and within certain embodiments, is capable of directing the expression of a nucleic acid molecule of interest. The retroviral vector must include at least one transcriptional promoter/enhancer or locus defining element(s), or other elements which control gene expression by other means such as alternate splicing, nuclear RNA export, post-translational modification of messenger, or post-transcriptional modification of protein. Such vector constructs must also include a packaging signal, long terminal repeats (LTRs) or portion thereof, and positive and negative strand primer binding sites appropriate to the retrovirus used (if these are not already present in the retroviral vector). Optionally, the recombinant retroviral vector may also include a signal which directs polyadenylation, selectable markers such as Neomycin resistance, TK, hygromycin resistance, phleomycin resistinacne histidinol resistance, or DHFR, as well as one or more restriction sites and a translation termination sequence. By way of example, such vectors typically include a 5' LTR, a tRNA binding site, a packaging signal, an origin of second strand DNA synthesis, and a 3' LTR or a portion thereof.

By "pseudotyping" or "psuedotyped," we mean that the genome and capsid proteins are from one retrovirus, while heterologous envelope glycoproteins are provided in trans by co-infection or co-transfection. In other words, a pseudotyped virus or vector displays heterologous envelope proteins encoded by another virus, and the pseudotype would exhibit the tropism of the complementing virus (the virus that provides the glycoproteins). The ability of non-SRV retrovirus such as MuLV, pseudotyped with the envelope nucleotide sequence of SRV, to infect monocytes and/or macrophages may require additional cis and/or trans acting functions of the SRV genome, for instance, the dUTPase enzyme. See Elder, *J. Virology* 66:1791–94(1992). By mutation analysis, this enzyme is found to confer the ability to infect nondividing cells upon certain retroviruses of non primate lentiviruses group, for example, equine infectious anemia virus, EIAV, (see Threadgill, *J. Virology* 67:2592–600(1993) and Lichtenstein, *J. Virology* 69:2881–88(1995), and other viruses, for example, herpes simplex virus type 1, HSV-1; see Pyles, *J. Virology* 66:6706–13(1992). Thus, the methods and compositions of the invention extends the tissue tropism of many retroviral vectors by enabling these vectors to infect cells that are normally not infectable by such vectors. Alternatively, such pseudotyping using the envelope protein of SRV can increase efficiency of gene transfer into lymphoid tissues. By providing a packaging cell line stably expressing gag-pol proteins from the non-SRV retrovirus along with transiently or stably expressed SRV-3 envelope protein, these abilities are conferred onto non-SRV retroviral vectors.

As noted above, the present invention provides recombinant retroviruses which are constructed to carry or express a selected nucleic acid molecule of interest. Briefly, numerous retroviral gene delivery vehicles may be utilized within the context of the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO 91/02805).

Particularly preferred recombinant retroviruses include those described in WO 91/02805.

Retroviral gene delivery vehicles of the present invention may be readily constructed from a wide variety of retroviruses, including for example, B, C, and D type retroviruses as well as spumaviruses and lentiviruses (see RNA Tumor Viruses, Second Edition, Cold Spring Harbor Laboratory, 1985). Preferred retroviruses for the preparation or construction of retroviral gene delivery vehicles of the present invention include retroviruses selected from the group consisting of Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Particularly preferred Murine Leukemia Viruses include 4070A and 1504A (Hartley and Rowe, *J. Virol.* 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Any of the above retroviruses may be readily utilized in order to assemble or construct retroviral gene delivery vehicles given the disclosure provided herein, and standard recombinant techniques (e.g., Sambrook et al, *Molecular Cloning: A Laboratory Manual*, 2d ed., Cold Spring Harbor Laboratory Press, 1989; Kunkle, *PNAS* 82:488, 1985). In addition, within certain embodiments of the invention, portions of the retroviral gene delivery vehicles may be derived from different retroviruses. For example, within one embodiment of the invention, retroviral vector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Within preferred aspects of the present invention, recombinant retroviruses may be made by introducing a vector construct as discussed above, into a cell (termed a "packaging cell") which contains those elements necessary for production of infectious recombinant retrovirus which are lacking in the vector construct. A wide variety of retroviral vector constructs may be utilized within the present invention in order to prepare recombinant retroviruses. For example, within one aspect of the present invention retroviral vector constructs are provided comprising a 5' LTR, a tRNA binding site, a packaging signal, one or more heterologous sequences, an origin of second strand DNA synthesis and a 3' LTR, wherein the vector construct lacks gag/pol or env coding sequences. Briefly, Long Terminal Repeats ("LTRs") are subdivided into three elements, designated U5, R and U3. These elements contain a variety of signals which are responsible for the biological activity of a retrovirus, including for example, promoter and enhancer elements which are located within U3. LTRs may be readily identified in the provirus due to their precise duplication at either end of the genome. As utilized herein, a 5' LTR should be understood to include a 5' promoter element and sufficient LTR sequence to allow reverse transcription and integration of the DNA form of the vector. The 3' LTR should be understood to include a polyadenylation signal, and sufficient LTR sequence to allow reverse transcription and integration of the DNA form of the vector.

The tRNA binding site and origin of second strand DNA synthesis are also important for a retrovirus to be biologically active, and may be readily identified by one of skill in the art. For example, retroviral tRNA binds to a tRNA binding site by Watson-Crick base pairing, and is carried with the retrovirus genome into a viral particle. The tRNA is then utilized as a primer for DNA synthesis by reverse transcriptase. The tRNA binding site may be readily identified based upon its location just downstream from the 5' LTR. Similarly, the origin of second strand DNA synthesis is, as its name implies, important for the second strand DNA synthesis of a retrovirus. This region, which is also referred to as the poly-purine tract, is located just upstream of the 3' LTR. In addition to a 5' and 3' LTR, tRNA binding site, and origin of second strand DNA synthesis, certain preferred retroviral vector constructs which are provided herein also comprise a packaging signal, as well as one or more nucleic acid molecules (e.g., heterologous sequences), each of which is discussed in more detail below.

Within one aspect of the invention, retroviral vector constructs are provided which lack both gag/pol and env coding sequences. As utilized herein, the phrase "lacks gag/pol or env coding sequences" should be understood to mean that the retroviral vector does not contain at least 20, preferably at least 15, more preferably at least 10, and most preferably at least 8 consecutive nucleotides which are found in gag/pol or env genes, and in particular, within gag/pol or env expression cassettes that are used to construct packaging cell lines for the retroviral vector construct.

Packaging cell lines suitable for use with the above-described retroviral vector constructs may be readily prepared (see U.S. Ser. No. 08/240,030, filed May 9, 1994; see also WO 92/05266), and utilized to create producer cell lines (also termed vector cell lines or "VCLs") for the production of recombinant vector particles. Within particularly preferred embodiments of the present invention packaging cell lines are made from human (e.g., HT1080 cells) or mink parent cell lines, thereby allowing production of recombinant retroviruses that are capable of surviving inactivation in human serum.

Accordingly, in one aspect, the invention comprises recombinant non-SRV retroviral vectors pseudotyped with the env gene product of a simian retrovirus. Preferably the nucleotide sequence encoding env protein employed is from SRV-3, although a nucleotide sequence encoding an env protein of any SRV could alternatively be used. Exemplary are the nucleotide sequences encoding env protein of SRV-1, SRV-2, SRV-4 and SRV-5.

Alternatively, the entire coding sequence of the env gene of SRV need not be used. A portion of an SRV env-encoding nucleotide sequence can be exchanged with an envencoding nucleotide sequence of another retrovirus (for example, MuLV) to introduce a desirable feature of the SRV-3 env partial sequence, for example, the SRV-3 env receptor binding or fusogenic domain.

It should be recognized that the present invention does not involve the use of any materials not previously available. For instance, RNA vectors (usually in DNA form) encoding MuLV LTR and packaging signal regions in a non-MuLV protein or genetic control sequence located downstream from the packaging signal have previously prepared and publicly disclosed. Similarly, the use of helper constructs to provide the missing gag and pol gene products is well known, as is the provision of env proteins from another source on a second helper construct. However, use of SRV env proteins has not previously resulted in infection of cells. Accordingly, the combination of a first vector having a coding region encoding MuLV LTR and packaging signal regions and a non-MuLV protein or genetic control sequence, the non-MuLV sequence being located downstream from the packaging signal; a second vector having a coding region encoding MuLV capsid proteins; and a third vector having a coding region encoding SRV envelope glycoproteins, was not known to provide a useful system for producing recombinant viral particles because of the lack of infectivity or any other proposed utility of the combination. The present invention therefore provides a new combination, in which any of the individual vectors can optionally be incorporated into a chromosome of the cell in which they are located; alternatively, the vectors can be provided as separate plasmids or any combination thereof. The pseudotype vector virus particles produced by the cell modified to contain the various vectors as described above itself comprises, as viral RNA in the particle, a recombinant vector comprising MuLV LTR and packaging signal regions and further comprising a coding region encoding a non-MuLV protein or genetic control sequence located downstream from the packaging signal; as capsid proteins, MuLV capsid proteins; and as envelope glycoproteins, SRV envelope glycoproteins.

The recombinant retroviral vectors of the invention optionally include a desired gene or gene fragment, or more than one gene or gene fragment. Such genes and/or gene fragments can comprise any sequence useful in gene therapy or for any other purpose (including simple cloning or product production). See e.g. WO96/21014, WO91/02805 for a description of nucleic acid sequences of therapeutic interest that can be introduced into the retroviral vectors of the invention. The desired gene or gene fragments are usually non retroviral sequences that are inserted into the retroviral vectors of the invention. However, in some cases the desired therapeutic gene may be a retoviral gene, e.g. a sequence encoding an HIV structural protein capable of inducing an anti-HIV immune response. In this later case the retroviral sequences are generally recombinant or heterologous to the retroviral vector (e.g. an HIV-1 therapeutic gene sequence is inserted into a MuLV vector).

For example, to enhance the body's natural cytotoxic defense mechanisms, recombinant MuLV vectors of the invention may include sequences which stimulate the production of, or genetically modify, tumor infiltrating lymphocytes (TIL). TIL transduced ex vivo with a retroviral vector expressing neo gene have been employed to study their homing sites in the human hosts. Similarly, TIL transduced with tumor necrosis factor (TNF) have been used to treat human patients with advanced melanoma. In addition, TIL transduced with chimeric T cell receptor (TcR) consisting of the constant region of the TcR and the variable region of a monoclonal antibody can be redirected to lyse cancer recognized by the monoclonal antibody.

The nucleic acid sequence inserted into the retroviral vector can be a viral structural gene that is capable of inducing an immune response against a viral infection. In the particular case of disease caused by HIV infection, where immunostimulation is desired, the antigen generated from a recombinant retrovirus may be in a form which will elicit either or both an HLA class I- or class II-restricted immune response. In the case of HIV envelope antigen, for example, the antigen is preferably selected from gp 160, gp 120, and gp 41, which have been modified to reduce their pathogenicity. In particular, the selected antigen is modified to reduce the possibility of syncytia, to avoid expression of epitopes leading to a disease enhancing immune response, to remove immunodominant, but haplotype-specific epitopes or to present several haplotype-specific epitopes, and allow a response capable of eliminating cells infected with most or all strains of HIV. The haplotype-specific epitopes can be further selected to promote the stimulation of an immune response within an animal which is cross-reactive against other strains of HIV. Antigens from other HIV genes or combinations of genes, such as gag, pol, rev, vif, nef, prot, gag/pol, gag prot, etc., may also provide protection in particular cases. HIV is only one example. This approach should be effective against many virally linked diseases or cancers where a characteristic antigen (which does not need to be a membrane protein) is expressed, such as in HPV and cervical carcinoma, HTLV-I-induced leukemias, prostate-specific antigen (PSA) and prostate cancer, mutated p53 and colon carcinoma and melanoma, melanoma specific antigens (MAGEs), and melanoma, mucin and breast cancer.

A variety of cytokine or immunomodulatory genes may be inserted into the retroviral vectors of the invention. Representative examples of such cytokines, such as IL-1, IL-2 (Karupiah et al., *J. Immunology* 144:290–298, 1990; Weber et al., *J. Exp. Med.* 166:1716–1733, 1987; Gansbacher et al., *J. Exp. Med.* 172:1217–1224, 1990; U.S. Pat. No. 4,738,927), IL-3, IL-4 (Tepper et al., *Cell* 57:503–512, 1989; Golumbek et al., *Science* 254:713–716, 1991; U.S. Pat. No. 5,017,691), IL-5, IL-6 (Brakenhof et al., *J. Immunol.* 139:4116–4121, 1987; WO 90/06370), IL-7 (U.S. Pat. No. 4,965,195) , IL-8, IL-9, IL-10, IL-11, IL-12, IL-13 (*Cytokine Bulletin*, Summer 1994), IL-14 and IL-15, particularly IL-2, IL-4, IL-6, IL-12, and IL-13, alpha interferon (Finter et al., *Drugs* 42(5):749–765, 1991; U.S. Pat. No. 4,892,743; U.S. Pat. No. 4,966,843; WO 85/02862; Nagata et al., *Nature* 284:316–320, 1980; Familletti et al., *Methods in Enz.* 78:387–394, 1981; Twu et al., *Proc. Natl. Acad. Sci. USA* 86:2046–2050, 1989; Faktor et al., *Oncogene* 5:867–872, 1990), beta interferon (Seif et al., *J. Virol.* 65:664–671, 1991), gamma interferons (Radford et al., *The American Society of Hepatology* 20082015, 1991; Watanabe et al., *PNAS* 86:9456–9460, 1989; Gansbacher et al., *Cancer Research* 50:7820–7825, 1990; Maio et al., *Can. Immunol. Immunother.* 30:34–42, 1989; U.S. Pat. No. 4,762,791; U.S. Pat. No. 4,727,138), G-CSF (U.S. Pat. Nos. 4,999,291 and 4,810,643), GM-CSF (WO 85/04188), tumor necrosis factors (TNFs) (Jayaraman et al., *J. Immunology* 144:942–951, 1990), CD3 (Krissanen et al., *Immunogenetics* 26:258–266, 1987), ICAM-1 (Altman et al., *Nature* 338:512–514, 1989; Simmons et al., *Nature* 331:624–627, 1988), ICAM-2, LFA-1, LFA-3 (Wallner et al., *J. Exp. Med.* 166(4):923–932, 1987), MHC class I molecules, MHC class II molecules, B7.1–.3, $\beta_2$-microglobulin (Parnes et al., *PNAS* 78:2253–2257, 1981), chaperones such as calnexin, MHC linked transporter proteins or analogs thereof (Powis et al., *Nature* 354:528–531, 1991).

Within one embodiment, the gene encodes gamma-interferon. Immunomodulatory factors may also be agonists, antagonists, or ligands for these molecules. For example soluble forms of receptors can often behave as antagonists for these types of factors, as can mutated forms of the factors themselves. Genes encoding any of the cytokine and immunomodulatory proteins described herein can be expressed in a retroviral vector to achieve long term in vivo expression. Other forms of these cytokines which are know to those of skill in the art can also be used. For instance, nucleic acid sequences encoding native IL-2 and gamma-interferon can be obtained as described in U.S. Pat. Nos. 4,738,927 and 5,326,859, respectively, while useful muteins of these proteins can be obtained as described in U.S. Pat. No. 4,853, 332. As an additional example, nucleic acid sequences encoding the short and long forms of mCSF can be obtained as described in U.S. Pat. Nos. 4,847,201 and 4,879,227, respectively. Retroviral vectors expressing cytokine or immunomodulatory genes can be produced as described herein and in PCT publication number U.S. Ser. No. 94/02951 entitled "Compositions and Methods for Cancer Immunotherapy". A variety of different forms of IGF-1 and IGF-2 growth factor polypeptides are also well known the art and can be incorporated into retroviral vectors for long term expression in vivo. See e. g. European Pat. No. 0123228B1, grant published on Sept. 19, 1993, entitled "Hybrid DNA Synthesis of Mature Insulin-like Growth Factors". As an additional example, the long term in vivo expression of different forms of fibroblast growth factor can also be effected by the methods of invention. See, eg. U.S. Pat. No. 5,464,774, issued Nov. 7, 1995, U.S. Pat. No. 5,155,214, and U.S. Pat. No. 4,994,559, for a description of different fibroblast growth factors.

As additional examples, Factor VIII or Factor IX is useful for treatment of blood clotting disorders, such as hemophilia. Different forms of Factor VIII, such as the B domain deleted Factor VIII construct described in WO 96/21014 can be used to produce retroviral vectors expressing Factor VIII for use in the methods of the invention. In addition to clotting factors, there are a number of proteins which can be expressed in the retroviral vectors of the invention and which are useful for treatment of hereditary diseases. These include lactase for treatment of hereditary lactose intolerance, AD for treatment of ADA deficiency, and alpha-1 antitypsin for treatment of alpha-1 antitrypsin deficiency. See F. D. Ledley, J. Pediatrics, 110, 157–174 (1987); I. Verma, Scientific American (November, 1987) pp. 68–84; and PCT Publication WO 9527512 entitled "Gene Therapy Treatment for a Variety of Diseases and Disorders" for a description of gene therapy treatment of genetic diseases.

Alternatively, the recombinant retroviral vectors of the invention may include inducible genes encoding toxic products or genes which confer sensitivity to a toxic drug (suicidal vector approach). An example of a gene encoding a toxic product is the diphtheria toxin gene. An example of a gene that confers sensitivity to a toxic drug is the herpes simplex virus tk gene, which enhances the capacity of cells to metabolize and incorporate nucleoside analogs such as acyclovir and ganciclovir. A variety of other prodrug converting enzymes can also be used in the retroviral vectors of the invention. See, for example, WO 95/14091 and EP 0 415 731 for a description of viral thymidine kinase and other prodrug converting systems for use in the retroviral vectors of the invention.

The recombinant MuLV vectors of the invention may include sequences, genes and/or gene fragments that encode either wild type or mutant forms of HIV or HTLV-I regulatory proteins or response elements that are required for virus production (for example, gag and rev proteins and TAR sequence of HIV) These sequences may be modified by the addition, substitution, or deletion of nucleotides to change the reading frame of the protein or by N- or C-terminal truncation or deletion of an internal sequence of nucleotides to result in the expression of a trans dominant or competing defective HIV or HTLV-I protein or response element. Delivery of the recombinant MuLV vectors of the invention carrying these wild type, defective or trans dominant-acting mutant sequences would "arm" the transduced cells with "decoy" proteins to either directly inhibit the replication of the infecting virus or to cause replication incompetency and abortive infection by the packaged virion particles.

Alternatively, the recombinant MuLV vectors of the invention may include sequences coding for antisense RNA or ribozyme against HIV or HTLV-I that specifically inhibit virus replication and would therefore find use in therapeutic and probably the prophylactic treatments for HIV or HTLV-I infection.

Significantly, the retroviral MuLV vectors of the invention may include sequences, genes and/or gene fragments to treat genetic diseases resulting from the expression of defective gene product/s such as severe combined immunodeficiency, chronic granulomatosis, Gaucher disease, sickle cell anemia, a- and b-thalasemias, Lesch-Nyhan syndrome, duchenne muscular distrophy, parkinson disease, emphysema, cystic fibrosis, phenylketonuria, familial hypercholesterolemia or hemophilia A and B. Table I below lists the deficient gene product and affected cell type which results in such disease states.

TABLE 1

| Genetic disease | deficient gene product | cell type(s) |
|---|---|---|
| Severe combined immunodeficiency | adenosine deaminase | T and B lymphocytes |
| Chronic granulomatosis | cytochrome b | Neutrophils |
| Gaucher disease | Glucocerebrosidase | Macrophage |
| Sickle cell anemia | β-globin | Erythrocyte |
| α- and β-thalasemias | α- and β-globin | Erythrocyte |
| Lesch-Nyhan syndrome | Hypoxanthine phosphoribosyl transferase | Basal ganglia |
| Duchenne muscular distrophy | Dystrophin | Muscle cells |
| Parkinson disease | Dopamine | Substania nigra |
| Phenylketonuria | Phenylalamine hydroxylase | Hepatocytes |
| Familial hypercholesterolemia | Low-density lipoprotein | Hepatocytes |
| Hemophilia A and B | Factors VIII and IX | Secretory products to be produced from endothelial cells |

Within the recombinant retroviral vectors of the invention, the desired sequences, genes and/or gene fragments can be inserted at several sites and under different regulatory sequences to check for optimal and stable expression. For example, a site for insertion can be the viral enhancer/promoter proximal site (i.e., 5'LTR-driven gene locus). Alternatively, the desired sequences can be inserted into the viral promoter distal site, where the expression of the desired sequence or sequences is through splicing of the promoter proximal cistron, an internal heterologous promoter as SV40 or CMV, or an internal ribosome entry site (IRES).

The retroviral vectors of the invention may additionally include a marker sequence(s) or marker gene(s) which encode(s) a protein conferring antibiotic resistance or which provide a molecular tag on transduced cells to permit their isolation by positive selection or by cell sorting devices. Examples of antibiotic resistance include the aminoglycoside phosphotransferase gene which is encoded by neo (aph) and confers resistance to neomycin or G418 (Southern, *J. Mol. Appl. Gen.* 1:327(1982)), and the hygromycin-B-phosphotransferase gene which is encoded by hyg (hph) and confers resistance to hygromycin-B (Gritz, *Gene* 25:179 (1983); Sugden, *Mol. Cell. Biol.* 5:410(1985); Palmer, *Proc. Natl. Acad. Sci. USA* 84:1055(1987)). Exemplary molecular tags include chimeric or wild type CD8 proteins and the nucleotide sequences encoding such proteins.

Nucleic acid molecules that encode the above-described substances, as well as other nucleic acid molecules that are advantageous for use within the present invention, may be readily obtained from a variety of sources, including for example depositories such as the American Type Culture Collection (ATCC, Rockville, Md.), or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), ATCC No. 39656 (which contains sequences encoding TNF), ATCC No. 20663 (which contains sequences encoding alpha interferon), ATCC Nos. 31902, 31902 and 39517 (which contains sequences encoding beta interferon), ATCC No. 67024 (which contains a sequence which encodes Interleukin-1b), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6).

Alternatively, cDNA sequences for use with the present invention may be obtained from cells which express or contain the sequences. Briefly, within one embodiment mRNA from a cell which expresses the gene of interest is reverse transcribed with reverse transcriptase using oligo dT or random primers. The single stranded cDNA may then be amplified by PCR (see U.S. Pat. Nos. 4,683,202, 4,683,195 and 4,800,159. See also *PCR Technology: Principles and Applications for DNA Amplification*, Erlich (ed.), Stockton Press, 1989) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA. Nucleic acid molecules which are carried and/or expressed by the recombinant retroviruses described herein may also be synthesized, for example, on an Applied Biosystems Inc. DNA synthesizer (e.g., APB DNA synthesizer model 392 (Foster City, Calif.).

In yet another aspect, the invention comprises methods of treating diseases caused by genetic lesions where there is expression of defective or deficient gene products, viral infections, tumors and cancers. In the method of treatment of the invention, MuLV vectors pseudotyped with SRV sequences will be used to infect target cells in an ex vivo or in vivo setting.

And yet another aspect of the invention, the virus vector particles can be used to produce any non-retroviral vector sequence specifically for the purpose of reproduction of that sequence, for example in the process of cloning sequences. In this sense, the virus particle acts simply as a cloning vehicle and has utility as such for the reproduction of any heterologous sequence that can be packaged into the viral particle, a matter that is readily determined by the ability of the system described herein to produce viral particles that infect other cells and thus reproduce.

It should be recognized that the following examples describe the use of materials that are not essential to the practice of invention. In particular, it is the opinion of the inventors that the particular vector systems, plasmids, and starting materials described in these examples can be replaced by any of numerous other commercially available vectors, plasmids, and other source materials with equal or better results than those described herein. There are continuing developments in the field of commercial vectors, and better performing vectors are constantly being prepared and made available. No attempt was made in the actual work carried out by the inventors to optimize the present invention. The inventors merely used systems that were readily available to them in their own laboratory or through other readily available sources. Using the guidance provided herein, any of the commercially or otherwise publicly sources of material could be selected with an expectation of similar or better results. It is the combination of material types that provides the present invention, not the use of a particular source.

All patents, patent applications, patent publications, and scientific publications cited herein are hereby incorporated by reference.

EXAMPLES

The various aspects of the invention summarized above are illustrated by the construction of p6c-SRVenv#f, a mammalian expression vector containing CMV enhancer and promoter regions driving the expression of the full sequence of SRV-3 env. More specifically, the p6c-SRVenv#f plasmid carries an insert comprising the entire envelope protein coding region, nucleotide (N) # 6242 (env ATG codon) through N # 8003 (env TAG stop codon), of the SRV-3 env sequence. The numbering system used herein for the SRV-3 env sequence (MPMV) is that of the 6A clone which is present in the Genebank sequence file SIVMPCG (accession number M12349). This numbering system differs from that in the publication describing the SRV-3 env sequence (Sonigo, P., Barker, C., Hunter, E., and Wain, H. S., 1986, *Cell* 45:375–85). The Genebank sequence has an additional LTR, between N # 416 and #743, which was deleted in the version published by Sonigo et al. in Cell, supra.

Plasmid p6c-SRVenv#f serves in this example as a helper construct to package MuLV vectors into SRV envelope pseudotyped vector particles, by providing the simultaneous presence of MuLV gag-pol encoded proteins. These proteins may be expressed by cotransfection of the nucleotide sequences encoding them into the cell containing the MuLV vector system. Alternatively, introduction of these sequences may be accomplished by using cell lines stably expressing these proteins. The plasmid p6c-SRVenv#f additionally includes ampicillin resistance gene for selection of bacterial transformants.

The molecular manipulations which resulted in the construction of p6c-SRVenv#f were initiated by making a deletion in the vector pSURE RT ARM #1. This vector, which is described in detail in Example 1, contains the C-terminus of the SRV-3 env nucleotide sequence, the 3' non-translated region and the 3' long terminal repeat (LTR) sequence. The deletion removed the 3' LTR and non-translated region present downstream of the SRV-3 env stop codon. The resulting vector, called pRtΔBE #1, contain the C-terminal coding region of the SRV-3 env nucleotide sequence, beginning with N # 7886 (Hind III site) at the 5' end of the fragment and ending at the N # 8000–8002 (TAGenv stop codon), followed by a 3' filled in Bgl II site. pRtABE #1 also contained a Xho I site 5' to the Hind III site. A fragment containing the remaining N-terminal portion of the SRV-3 env nucleotide sequence, from N # 6242 (ATG env start codon) to N # 7886 (Hind III site) was excised from the vector pTGHX1 using 3' Hind III and 5' mutagenesis-introduced Xho I restriction sites and was subcloned into the 3' Hind III and 5' Xho I restriction sites in plasmid pRTΔBE #1 to restore the entire env coding sequence in the correct reading orientation. The entire sequence was then subcloned into pCMV6c, to generate p6c-SRVenv#f.

Alternatively, the env coding region of SRV-3 can be excised from other plasmid vectors known in the art to contain it, for example, pSHRM15 (see Rhee, S. S., Hui, H. and Hunter, E., 1990, *J. Virol.* 64(8):3844–52) and subcloned into an appropriate mammalian expression vector. Thus, the invention is not limited by the heterologous material incorporated into the vector, and the reproduction system can be used within any cell line that can be infected by SRV.

The env-expressing plasmid p6c-SRVenv#f was then co-transfected with plasmid pLNPOZ, a MuLV based retroviral vector, into a derivative of the 293 cell line, a transformed primary human embryonal kidney cell line. The derivative cell line, 293-2-3, stably expresses the gag-pol nucleotide sequences of MuLV. Supernatants from these transfected cells were used in infection studies described in detail in the following examples. Briefly, the infected cells were tested for the presence of the p6c-SRVenv#f plasmid in a beta-galactosidase assay and/or by G418 selection.

Successful pseudotyping of MuLV based pLNPOZ and AP-Puro vectors with the SRV-3 env protein was demonstrated by showing the capability of these pseudotyped vector preparations to infect 293, 293-2-3, HT1080, and Raji cells. As expected, the murine 3T3 cell line was incapable of infection with the SRV-3 pseudotyped vector.

SOURCE OF MATERIALS USED IN EXAMPLES

The source of all SRV-3 sequences was the infectious molecular clone, pMPMV6A/7 (Barker, C. S., Pickel, J., Tainsky, M. and Hunter, E., 1986, *Virology* 153:201–14). pSHRM15 is an expression plasmid which carries the full length and colinear integrated provirus, pMPMV6A/7 (Rhee, S. S., Hui, H. and Hunter, E., 1990, *J. Virol.* 64(8):3844–52). pTGHSXI has been derived from pSHRM15 and carries SRV-3 region from N # 880(Hha I site) to N # 8373 (Sph I site) cloned into EcoR I and Sph I sites of pTG90 (polylinker derived from pSP72); pTGHSXI thus carries the entire coding region and part of the 3' LTR of the SRV-3. In addition, a Xho I site has been introduced by site specific mutagenesis at the junction of pol and env genes (position 5815). The construction of pSURE RT ARM #1 has been described in the Ph. D dissertation by Khan, M. A., 1994, entitled "Gene Transfer Vectors Based on the Simian Type-D Retrovirus", available from the Shields Library, University of California at Davis, Davis, Calif. 95616. pSURE RT ARM #1 contains N # 7886 (Hind III) to N # 8557 (3' end) of the SRV-3 genome and thus possesses C-terminus env, 3' untranslated region and 3' LTR. pSURE RT ARM #1 contains the Xho I site of the pSP72 polylinker (Promega Corporation) which is adjacent to the Hind III site used for cloning SRV-3 region described above; EcoR V and Cla I restriction sites of the pSP72 polylinker are adjacent to EcoR I site. In addition, a Bgl II site introduced immediately downstream (N # 8001–8006) of env TAG stop codon (N # 8000–8002) is present in pSURE RT ARM #1. pCMV6c was obtained from Chiron Corporation (Barbara Chapman). pCMV6c is a mammalian expression vector which allows subcloning of gene of interest under the transcriptional control of the immediate early promoter/enhancer region of the human cytomegalovirus (hvCMV-IE1) which is constitutively expressed in mammalian cells.

p6c-ampho env #8 and pMLPG (Chrion Viagene Inc.) are mammalian expression vectors used as positive controls for different experiments. p6c-ampho env #8 has a vector background identical to p6c-SRVenv#f and it expresses amphotropic env gene. Amphotropic env gene was cloned as a Xba I fragment of pAM7 (Chiron Viagene Inc.) into same restriction site of pCMV6c to generate p6c-ampho env #8. pMLPG expresses vesicular stomatitis virus G protein (VSVG) under the transcriptional regulation of adenovirus late promoter.

MuLV based retroviral vectors used for these studies were pLNPOZ and pSEAP-Puro. pLNPOZ was obtained from Dr. A. Dusty Miller of the Fred Hutchinson Cancer Research Center in Seattle, Wash. 98104. pLNPOZ is a bicistronic vector containing promoter proximal neo gene encoding for neomycin resistance and the promoter distal b-galactosidase gene under the regulation of the 5' non translated region of poliovirus providing internal ribosome entry site (IRES). pSEAP-Puro was provided by Dr. Klaus Giese of Chiron Corporation. This vector confers puromycin resistance and ability to make secretory form of alkaline phosphatase (SEAP) on transfected or infected cells.

Example 1

Construction of p6c-SRVenv#f: An SRV-3 env Expressing Vector for Mammalian Cells The following molecular manipulations were done to restore minimum length SRV-3 env gene and to express transiently the SRV-3 protein in mammalian cells. pSURE RT ARM #1 was first digested with Bgl II and EcoR I restriction enzymes and then subjected to a T4 DNA polymerase fill-in reaction. The larger DNA fragment was gel purified and its blunt ends were ligated. The resulting construct, pRtABE #1, has a deletion removing 3' LTR and 3' untranslated region downstream of the SRV-3 env stop codon. However, pRtABE #1 retains the C-terminus env region spanning from N # 7886 (Hind III) to N # 8002 (env stop codon). This deletion also brought the EcoR V and Cla I restriction sites of the polylinker next to (3' to) the env stop codon. Using the mutagenesis introduced 5' Xho I and 3' Hind III restriction sites (4th Hind III on SRV-3 genome) of pTGHSXI, a fragment containing 5' region of SRV-3 env gene (N-terminus) was gel purified and subcloned into same restriction sites of pRtABE #1 to make pSRVenv#1. Minimum length SRV-3 env gene was thus restored in pSRVenv#1.

pCMV6c, a mammalian expression vector was digested with Bcl I and treated with T4 DNA polymerase to create blunt ends and was further digested with Sal I and gel purified. A 5' Xho I and 3' EcoR V digested fragment of pSRVenv#1 carrying the SRV-3 env was then gel purified and ligated into the 5' Sal I and 3' Bcl I blunt ended fragment of pCMV6c to generate the vector p6c-SRVenv#f.

Cell Cultures

The following cell lines were obtained from ATCC: 293 cells are transformed primary human embryonal kidney cells (ATCC CRL 1573); Raji cells are B lymphoblastlike cells derived from a human Burkitt lymphoma (ATCC CCL 86); HT1080 cell line is derived from human fibrosarcoma (ATCC CCL 121); 3T3-Swiss albino cell line was derived form Swiss mouse embryonic tissue (ATCC CCL 92); HeLa is an aneuploid epithelial like cell line derived from a human cervical carcinoma (ATCC CCL 2).

293-2-3 is a derivative of 293 which stably expresses gag-pol genes of MuLV and was obtained from Viagene Inc. Generation of the pLN cells from 293-2-3 cells is described in the section below, "Analysis For Infective Capacity". SRV-3-HeLa and SRV-3-HT1080 are SRV-3 infected cell lines described in the section, "Studies to verify SRV-3 env pseudotypes: cell tropism and viral interference."

All cell cultures were grown using tissue culture incubators at 37° C. with 7–10% $CO_2$ and hydrated environment. Raji and other non-adherent cell lines were maintained on RPMI 1640 medium (Catalog 51501-78P, Bio Sciences, Lenexa, KS 66215) supplemented with 10% heat inactivated fetal bovine serum, dialyzed (catalog # A-1101-L, HyClone Laboratories, Inc. 1725 South HyClone Road, Logan, Utah 84321), 100 units/ml of penicillin, and 100 ug/μl of Streptomycin. 293, 293-2-3, pLN, HT1080, SRV-3-HT1080, and 3T3-Swiss albino cells were grown on DMEM/high modified medium (Catalog # 51441-78P, Bio Sciences, Lenexa, Kans. 66215) supplemented with 10% heat inactivated fetal bovine serum, dialyzed, 100 units/ml of penicillin, and 100 mg/ml of Streptomycin. HeLa and SRV-3-HeLa cells were propagated on EMEM medium (Catalog # 51411-78P, Bio Sciences, Lenexa, Kans. 66215) supplemented with 10% heat inactivated fetal bovine serum, dialyzed, 100 units/ml of penicillin, and 100 μg/ml of Streptomycin. For antibiotic selection experiments, stock solutions of different antibiotics (for example, G418) were prepared, filtered through 0.2 mm filters, and stored at manufacturers recommended temperatures. Antibiotics were added to the fresh culture medium with final concentrations in working range depending on the cell type and antibiotics used. Selection media thus prepared were used to feed the trypsinized cells after 48 hours post-transfection or post-infection and thereafter every 48–72 hours until the antibiotic resistant colonies appeared.

Pseudotyping of MuLV based retroviral vector with SRV-3 helper construct: (pseudotype experiments)

All the DNA transfections carried out for the pseudotype experiments were based on the calcium phosphate precipitation method (Graham, F. L. and van der Eb, A. J., 1973, *Virology* 52:456; Wigler, M. et al., 1977, *Cell* 11:223). Reagents used for calcium phosphate mediated transfection were from Promega kit (Catalog # E1200: ProFection Mammalian Transfection System-Calcium Phosphate, Promega Corporation, 2800 Woods Hollow Road, Madison, Wis. 53711) and the protocol followed was according to manufacturer's instructions (Part # TM012, revised October 1994: Technical Manual, Profection Mammalian Transfection Systems). DNA samples employed for transfections were prepared by alkali lysis method and were purified either by cesium chloride ultracentrifugation to equilibrium twice or were passed through columns (Qiagen-tip 500 anion-exchange resin included in Qiagen kit, catalog # 12162 and 12163 for Maxi preps; Qiagen Inc., Chatsworth, Calif. 91311).

For pseudotyping MuLV retroviral vector with SRV3 envelope, 293-2-3 cells were cotransfected with p6c-SRVenv#f and MuLV vector. This allowed packaging of the transiently expressed full length MuLV vector RNA into the stably expressed MuLV gag-prt-pol particles which acquired the viral envelope (concentrated with SRV envelope proteins) following budding through cell membrane. (Positive control consisted of p6c-Ampho env#8 and pMLPG. 293-2-3 cells not receiving any env expressing plasmids were the negative control). Following transfections, supernatants containing the pseudotyped MuLV vectors were harvested, passed through 0.45 μm filters, and were kept frozen at 75° C. until use for infections.

About 16 to 24 hours before starting the infection, stock cultures of different adherent cell lines were digested with trypsin and appropriate number of cells (0.5–1×10$^6$) were seeded into six-well plates containing about 4.5 ml of appropriate culture medium. Frozen vials of the vector preparations as described above were thawed at 37° C. Culture medium from the semi-confluent cell cultures were aspirated and 0.5–1 ml of the different filtered supernatants were added to appropriately marked cell cultures in the six-well plates. Polybrene was added to a final concentration of 8 mg/ml. Plates were then incubated for 1–2 hours at room temperature on a rocking devise using gentle motion. Vector supernatants were aspirated and the cells were feed with fresh media and incubated for 48 hours at 37° C. incubator with 7–10% CO2 and hydrated environment. Infected cells were then monitored for the presence of vector by different marker rescue assays described below.

Analysis For Infective Capacity

In experiments using pLNPOZ vector, transfected or infected target cells were studied for the expression of reporter gene lac Z (β-gal. assay) or by subjecting the cells to a positive selection (G418) against the neo marker. Presence of the vector in infected cells was studied by marker rescue experiments including β-galactosidase enzyme production monitored by in situ staining reactions using the enzymes chromogenic substrate, X-gal. Using variable concentrations of G418 (ranging from final concentrations 200–1000 ug/ml of the active antibiotic), transfected or infected cells of different cell lines were selected for the vector expressing cells. pLN cell line was developed by infecting 293-2-3 cells with pLNPOZ vector pseudotyped with amphotropic envelope proteins and pooling the G418 resistant colonies following selection. pLN cells thus stably express MuLV based pLNPOZ vector in addition to MuLV gag-pol gene products and served as a useful reagent for pseudotyping experiments.

In experiments using AP-Puro vector, transfected or infected target cells were studied for the expression of reporter gene (alkaline phosphatase; AP-assay) or by subjecting the cells to a positive selection (puromycin). Presence of the vector in infected cells was measured by AP enzyme production.

Results of the pseudotype experiments

Successful pseudotyping of MuLV based vectors, pLN-POZ and AP-Puro vectors was demonstrated by showing marker rescue upon infection of susceptible primate cells, including 293, 293-2-3, HT1080, HeLa, and Raji cells. Marker rescue experiments involved transfer of G418 resistance and β-galactosidase activity for pLNPOZ vector and puromycin resistance and alkaline phosphatase (AP) activity AP-Puro vector. As expected, the murine 3T3 cell line was incapable of infection with the SRV3 pseudotyped vector.

Studies to verify SRV3 env pseudotypes: cell tropism and Viral Interference

Studies were initiated to verify that packaged vector particles pseudotyped with SRV3 env were indeed displaying SRV3 envelope glycoproteins and thereby SRV3 host and tissue tropism. By using in-situ staining for β-galactosidase, pLNPOZ vector pseudotyped with SRV3 env was found incapable of infecting murine 3T3 cells (unlike the positive control vectors displaying ecotropic or amphotropic envelope proteins). Viral interference studies were initiated to allow verification of the MuLV pseudotypes bearing SRV3 glycoproteins. Reagents for these studies were prepared by infecting HeLa and HT1080 cells in parallel with equal volumes of a filtered supernatant containing wild type SRV-3. Procedure for setting infection is described above and respective media were change every 48–72 hours. Infection was monitored by appearance of cytopathic effect, cpe, (multinucleated syncitia) in the HeLa cells. HeLa cells demonstrated extensive cpe; however no detectable cpe was observed with HT1080 cells. Aliquots of filtered supernatants were frozen down from both infected cultures to verify production of the virus on indicator Raji cells. Infected cells were further propagated and lost of cpe was observed in HeLa cells. These cells, however, were capable of inducing cpe when mixed and propagated with uninfected HeLa cells. At this stage, both cell lines were considered to be chronically infected with SRV-3, and were called SRV-3-HeLa and SRV-3-HT1080.

Amphotropic MuLV is known to bind a distinct cellular receptor and belongs to a different receptor interference group than SRV. Thus both the virus and the MuLV vector pseudotypes bearing amphotropic envelope proteins are expected to super-infect cells otherwise infected with SRV-3. SRV3 pseudotypes, on the other hand, are expected to be blocked for super-infection of cells chronically infected with SRV3 (phenomenon of viral interference to super-infection).

Both uninfected and SRV3 infected HeLa and HT1080 cells were used for viral interference studies and all the infections were set according to the procedure described above. Filtered supernatants containing pLNPOZ pseudotyped with SRV-3- or ampho env were used to super-infect SRV-3-HeLa or SRV-3-HT1080 cells; infection of the uninfected HeLa and HT1080 cells with equal volumes of the respective supernatants were done as positive controls. These pseudotypes infections were monitored by in-situ staining for β-galactosidase after 48 hours post-infection.

Results of the viral interference experiments

Both SRV-3- and amphotropic envelope proteins bearing pseudotypes of pLNPOZ vector successfully infected HeLa and HT1080 cells demonstrated by in-situ staining for β-galactosidase. However, the same assay failed to show super-infection of SRV-3-HeLa and SRV-3-HT1080 cells with SRV3 env pseudotypes; i.e., the cells remained negative for β-galactosidase activity. Amphotropic envelope bearing pseudotype of pLNPOZ, however, was found capable of infecting both SRV-3-HeLa and SRV-3-HT1080. These results were consistent with the predictions that viral interference would be exerted by SRV3 infection of the cells towards super-infecting vector particles displaying env glycoproteins of the same receptor interference group (homologous SRV3 env pseudotype) and not against super-infecting vector particles displaying env glycoproteins of the different receptor interference group (amphotropic env pseudotype).

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A cell producing recombinant retroviral particles, comprising:
    a first vector having a coding region encoding retroviral LTRs and a packaging signal under the control of an expression control system and a tRNA binding site located upstream from said packaging signal and origin of second strand DNA synthesis located downstream from said packaging signal,
    a second vector having a coding region encoding retroviral capsid proteins gag and pol under the control of an expression control system, and
    a third vector having a coding region encoding a simian type D retrovirus envelope glycoprotein under the control of an expression control system.

2. The cell of claim 1, wherein each of said expression control systems is different from one another.

3. A pseudotyped vector virus particle, comprising:
    as viral RNA in said particle, a recombinant viral vector comprising a packaging signal and further comprising a R region and a coding region encoding a tRNA binding site located unstream from said packaging signal and origin of second strand DNA synthesis and R region located downstream from said packaging signal;
    as capsid proteins, retroviral gag and pol capsid proteins;
    as envelope glycoproteins, simian type D retrovirus envelope glycoproteins.

4. The cell of claim 1, wherein said first vector lacks gag/pol or env coding sequences.

5. The cell of claim 1, wherein said first vector further includes a heterologous nucleic acid sequence encoding a selected biologically active product.

6. The cell of claim 4, wherein said first vector further includes a heterologous nucleic acid sequence encoding a selected biologically active product.

7. The cell of claim 6, wherein each of said vectors comprises a separate plasmid.

8. The cell of claim 6, wherein at least one of said vectors is incorporated into a chromosome of said cell.

9. The cell of claim 6, wherein at least one of said vectors is expressed episomally.

10. The particle of claim 3, wherein said recombinant viral vector lacks gag/pol or env coding sequences.

11. The particle of claim 3, wherein said recombinant viral vector further includes a heterologous nucleic acid sequence encoding a selected biologically active product.

* * * * *